United States Patent [19]

Moser

[11] Patent Number: 4,618,361
[45] Date of Patent: * Oct. 21, 1986

[54] ACYLAMIDES AND COMPOSITIONS FOR THE PROTECTION OF CULTIVATED PLANTS AGAINST THE PHYTOTOXIC ACTION OF HERBICIDES

[75] Inventor: Hans Moser, Magden, Switzerland

[73] Assignee: CIBA-GEIGY Corporation, Ardsley, N.Y.

[*] Notice: The portion of the term of this patent subsequent to Jul. 22, 2003 has been disclaimed.

[21] Appl. No.: 560,465

[22] Filed: Dec. 12, 1983

[51] Int. Cl.$^4$ .................. A01N 43/84; C07D 265/36; C07D 279/16

[52] U.S. Cl. ......................... 71/88; 47/57.6; 47/58; 71/90; 71/91; 71/92; 71/94; 71/95; 544/52; 544/58.2; 544/58.4; 544/105

[58] Field of Search .............. 544/52, 58.2, 105, 58.4; 71/88, 90, 91, 92, 94, 95; 47/57.6, 58

[56] References Cited

U.S. PATENT DOCUMENTS

| | | | |
|---|---|---|---|
| 3,547,915 | 12/1970 | Bub | 544/105 |
| 4,295,875 | 10/1981 | Eicken et al. | 71/88 |
| 4,322,240 | 3/1982 | Leach | 71/88 |

FOREIGN PATENT DOCUMENTS

| | | |
|---|---|---|
| 1952910 | 6/1970 | Fed. Rep. of Germany . |
| 1567075 | 7/1970 | Fed. Rep. of Germany . |
| 2141586 | 3/1972 | Fed. Rep. of Germany . |
| 2218097 | 11/1972 | Fed. Rep. of Germany . |
| 2245471 | 3/1973 | Fed. Rep. of Germany . |
| 2402983 | 8/1974 | Fed. Rep. of Germany . |
| 2828265 | 1/1980 | Fed. Rep. of Germany . |
| 2828293 | 1/1980 | Fed. Rep. of Germany . |
| 2021611 | 7/1970 | France . |
| 1277557 | 6/1972 | United Kingdom . |

OTHER PUBLICATIONS

Prasad, Chemical Abstracts, vol. 70 (1969) 106447m.
Babudri et al., J. Org. Chem. vol. 48(22), 1983 pp. 4082–4087.

Primary Examiner—Richard L. Raymond
Attorney, Agent, or Firm—Edward McC. Roberts; Kevin T. Mansfield

[57] ABSTRACT

The acylamide derivatives of the formula I below are suitable for use as a counter-agent, "antidote" or "safener" for protecting cultivated plants against the phytotoxic action of herbicides. Crops suitable in this respect are preferably millet, cereals, rice, maize and soya, and suitable herbicides are chloroacetanilides and thiolcarbamates.

The acylamide derivatives have the formula I

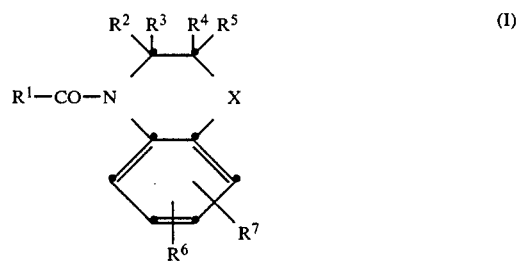

in which X is oxygen, sulfur, —SO— or —SO$_2$—; R$^1$ is C$_1$–C$_6$-halogenoalkyl, C$_1$–C$_6$-cyanoalkyl or C$_2$–C$_6$-halogenoalkenyl; R$^2$ and R$^5$ independently of one another are hydrogen, C$_1$–C$_4$-alkyl, C$_1$–C$_4$-halogenoalkyl, C$_2$–C$_4$-alkenyl, C$_2$–C$_4$-alkynyl or C$_2$–C$_4$-alkoxyalkyl; R$^3$ and R$^4$ independently of one another are hydrogen, C$_2$–C$_4$-alkenyl, C$_2$–C$_4$-alkynyl, cyano, C$_2$–C$_4$-alkoxyalkyl, —COOR$^8$, —CO—NR$^9$R$^{10}$ or C$_1$–C$_4$-alkyl which is unsubstituted or substituted by halogen, cyano or —CO—A; R$^6$ and R$^7$ independently of one another are hydrogen, halogen, C$_1$–C$_4$-alkyl, C$_1$–C$_4$-alkoxy, C$_1$–C$_4$-halogenoalkyl or C$_1$–C$_4$-halogenoalkoxy, A is C$_1$–C$_4$-alkyl, C$_2$–C$_4$-alkenyl, C$_1$–C$_4$-alkoxy, C$_3$–C$_4$-alkenyloxy, C$_3$–C$_4$-alkynyloxy or —NR$^{11}$R$^{12}$; R$^8$, R$^{10}$ and R$^{12}$ independently of one another are hydrogen, C$_1$–C$_4$-alkyl, C$_3$–C$_4$-alkenyl, C$_3$–C$_4$-alkynyl or C$_3$–C$_4$-alkoxyalkyl; and R$^9$ and R$^{11}$ independently of one another are hydrogen, C$_1$–C$_4$-alkyl, C$_3$–C$_4$-alkenyl, C$_1$–C$_4$-alkoxy, C$_3$–C$_4$-alkynyl or C$_3$–C$_4$-alkoxyalkyl, it being also possible for R$^9$ and R$^{10}$ and also R$^{11}$ and R$^{12}$, together with the nitrogen atom linking them, to form a 5-membered or 6-membered saturated heterocyclic structure which can, if desired, contain an oxygen or sulfur atom or an —NH— or —N(C$_1$–C$_4$-alkyl)- bridge as a member of the ring.

28 Claims, No Drawings

ACYLAMIDES AND COMPOSITIONS FOR THE PROTECTION OF CULTIVATED PLANTS AGAINST THE PHYTOTOXIC ACTION OF HERBICIDES

The present invention relates to a composition for the protection of cultivated plants against the phytotoxic action of herbicides, which contains, as the herbicide-antagonistic active substance, an acylamide derivative, and also to compositions already containing the herbicide as well as this antagonistic active substance, and to a process for selectively controlling weeds by means of a herbicide and this counter-agent. The invention also embraces new acylamide derivatives and the preparation thereof.

It is known that herbicides belonging to a very wide variety of classes of substances, such as triazines, urea derivatives, carbamates, thiolcarbamates, halogenoacetanilides, halogenophenoxyacetic acids etc., when applied in an effective dose, occasionally also damage the cultivated plants to a certain extent as well as the weeds to be controlled. Overdoses are often applied unintentionally and accidentally when verge zones overlap in the course of stripwise spraying, either through the action of the wind or as the result of the width of action of the spraying device being wrongly estimated. The climatic conditions or the nature of the soil can be such that the amount of herbicide recommended for normal conditions acts as an overdose. The quality of the seed can also affect toleration of the herbicide. In order to provide against this problem, various substances have already been suggested which are capable of antagonising in a specific manner the harmful action of the herbicide on the cultivated plant, i.e. protecting the cultivated plant, without thereby noticeably affecting the herbicidal action on the weeds to be controlled. In the course of this it has been found that the counter-agents suggested often act in a very species-specific manner relative to both the cultivated plants and the herbicide and, in some cases, also as a function of the mode of application, i.e. a specific counter-agent is often only suitable for a specific cultivated plant and a few classes of herbicidal substances.

Thus British Patent Specification No. 1,277,557 describes the treatment of seeds or shoots of wheat and sorghum with certain oxamic acid esters and amides to protect them against attack by "ALACHLOR" (N-methoxymethyl-N-chloroacetyl-2,6-diethylaniline). Counter-agents for treating cereal, maize and rice seeds to protect them against the harmful action of herbicidally active thiolcarbamates are suggested in German Offenlegungsschriften Nos. 1,952,910 and 2,245,471 and in French Patent Specification No. 2,021,611. Hydroxyaminoacetanilides and hydantoins are used in accordance with German Patent Specification No. 1,567,075 and U.S. Patent Specification No. 3,131,509 for the protection of cereal seed against carbamates.

The direct pre-emergence or post-emergence treatment of certain useful plants with counter-agents as antagonists of specific classes of herbicide on a cultivated area is described in German Offenlegungsschriften Nos. 2,141,586 and 2,218,097 and in U.S. Pat. No. 3,867,444. It is also possible, in accordance with German Offenlegungsschrift No. 2,402,983, to protect maize plants effectively against damage by chloroacetanilides, by applying an N-disubstituted dichloroacetamide to the soil as a counter-agent. Compounds of this type are also used in accordance with U.S. Patent Specification No. 4,137,070 as antidotes for herbicidal thiocarbamates or, in accordance with German Offenlegungsschriften Nos. 2,828,265 and 2,828,293, as antidotes against herbicidal acetanilides. It has now been found, surprisingly, that a group of acylamide derivatives is excellently suitable for protecting cultivated plants against the harmful action of agricultural chemicals, for example plant protection compositions, especially herbicides. In the following text, therefore, these acylamide derivatives are also described as "counter-agents", "antidotes" or "safeners".

Acylamide derivatives suitable for protecting cultivated plants against the harmful action of agricultural chemicals have the formula I

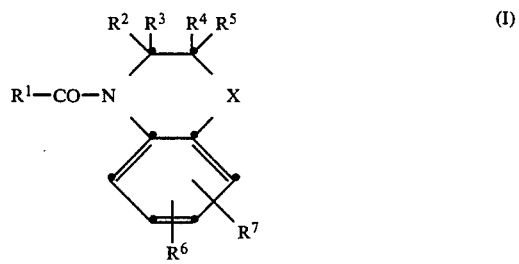

in which X is oxygen, sulfur, —SO— or —SO$_2$—; R$^1$ is C$_1$–C$_6$-halogenoalkyl, C$_1$–C$_6$-cyanoalkyl or C$_2$–C$_6$-halogenoalkenyl; R$^2$ and R$^5$ independently of one another are hydrogen, C$_1$–C$_4$-alkyl, C$_1$–C$_4$-halogenoalkyl, C$_2$–C$_4$-alkenyl, C$_2$–C$_4$-alkynyl or C$_2$–C$_4$-alkoxyalkyl; R$^3$ and R$^4$ independently of one another are hydrogen, C$_2$–C$_4$-alkenyl, C$_2$–C$_4$-alkynyl, cyano, C$_2$–C$_4$-alkoxyalkyl, —COOR$^8$, —CO—NR$^9$R$^{10}$ or C$_1$–C$_4$-alkyl which is unsubstituted or substituted by halogen, cyano or —CO—A; R$^6$ and R$^7$ independently of one another are hydrogen, halogen, C$_1$–C$_4$-alkyl, C$_1$–C$_4$-alkoxy, C$_1$–C$_4$-halogenoalkyl or C$_1$–C$_4$-halogenoalkoxy; A is C$_1$–C$_4$-alkyl, C$_2$–C$_4$-alkenyl, C$_1$–C$_4$-alkoxy, C$_3$–C$_4$-alkenyloxy, C$_3$–C$_4$-alkynyloxy or —NR$^{11}$R$^{12}$; R$^8$, R$^{10}$ and R$^{12}$ independently of one another are hydrogen, C$_1$–C$_4$-alkyl, C$_3$–C$_4$-alkenyl, C$_3$–C$_4$-alkynyl or C$_3$–C$_4$-alkoxyalkyl; and R$^9$ and R$^{11}$ independently of one another are hydrogen, C$_1$–C$_4$-alkyl, C$_3$–C$_4$-alkenyl, C$_1$–C$_4$-alkoxy, C$_3$–C$_4$-alkynyl or C$_3$–C$_4$-alkoxyalkyl, it being also possible for R$^9$ and R$^{10}$ and also R$^{11}$ and R$^{12}$, together with the nitrogen atom linking them, to form a 5-membered or 6-membered saturated heterocyclic structure which can, if desired, contain an oxygen or sulfur atom or an —NH— or —N(C$_1$–C$_4$-alkyl)-bridge as a member of the ring.

Insofar as optical isomers of compounds of the formula I exist, both the optically pure isomers and the mixtures of isomers are to be understood within the scope of the present invention.

Halogen itself in the definitions, and also halogen as a moiety in halogenoalkoxy, halogenoalkyl or halogenoalkenyl, is to be understood as meaning fluorine, chlorine, bromine and iodine, but preferably fluorine, chlorine and bromine and especially chlorine.

In the definitions, alkyl is to be understood as meaning linear or branched alkyl, for example: methyl, ethyl, n-propyl, i-propyl or the four isomeric butyls.

Alkoxy is to be understood as meaning: methoxy, ethoxy, n-propoxy, i-propoxy or the four isomeric butoxy radicals, but particularly methoxy, ethoxy or i-propoxy.

Examples of unsaturated substituents or parts of substituents are vinyl, vinyloxy, allyl, allyloxy, propargyl, propargyloxy, methallyl, methallyloxy, butenyl, butenyloxy, butynyl, butynyloxy, chlorovinyl, dichlorovinyl, trichlorovinyl, 3,3,3-trifluoro-1-propenyl, 3,3,3-trichloro-1-propenyl or 2,3-dichloropropargyl.

Alkoxyalkyl radicals are represented by methoxymethyl, ethoxymethyl, methoxyethyl and ethoxyethyl, but particularly methoxyethyl. Halogenoalkyl, as a substituent in its own right or as a part of another substituent, such as halogenoalkoxy or halogenoalkylthio, is generally chloromethyl, fluoromethyl, difluoromethyl, trifluoromethyl, dichloromethyl, trichloromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl, 2-chloropropyl, 1,1,2,3,3,3-hexafluoropropyl, 3,3,3-trichloropropyl, 2,2,2-trichloroethyl and 1-chloroethyl, but especially chloromethyl, dichloromethyl, trichloromethyl and 1-chloroethyl.

Herbicide antagonists which should be singled out because of their action are those in which either
(a) X is oxygen, or
(b) $R^1$ is $C_1-C_6$-halogenoalkyl or $C_2-C_6$-halogenoalkenyl, or
(c) $R^2$ and $R^5$ are hydrogen, or
(d) $R^3$ and $R^4$ independently of one another are hydrogen, $C_1-C_4$-alkyl, $C_1-C_4$-alkoxycarbonylmethyl or $C_1-C_4$-alkoxycarbonyl, or
(e) $R^6$ and $R^7$ independently of one another are hydrogen or $C_1-C_4$-alkyl.

Preferred active substances in subgroup b are those in which $R^1$ is $C_1-C_4$-halogenoalkyl, and preferred active substances in subgroup d are those in which $R^3$ and $R^4$ independently of one another are hydrogen or methyl.

A very particularly preferred group of active substances is that in which X is oxygen, $R^1$ is $C_1-C_6$-halogenoalkyl or $C_2-C_6$-halogenoalkenyl, $R^2$ and $R^5$ are hydrogen, $R^3$ and $R^4$ independently of one another are hydrogen, $C_1-C_4$-alkyl, $C_1-C_4$-alkoxycarbonylmethyl or $C_1-C_4$-alkoxycarbonyl and $R^6$ and $R^7$ independently of one another are hydrogen or $C_1-C_4$-alkyl.

Within this group in turn, preferred active substances are those in which $R^1$ is $C_1-C_4$-halogenoalkyl and $R^3$, $R^4$, $R^6$ and $R^7$ independently of one another are hydrogen or methyl.

The following preferred individual active substances should be mentioned: 4-dichloroacetyl-2,3-dihydro-3,5-dimethyl-1,4-benzoxazine, 4-dichloroacetyl-2,3-dihydro-3-methyl-1,4-benzoxazine or 4-(2-chloropropionyl)-2,3-dihydro-3-methyl-1,4-benzoxazine.

Most of the compounds of the formula I are novel. Some are described in the literature. Thus several halogenoalkanoyl amides are known as pharmaceutical active substances or intermediates for substances having a pharmaceutical action from British Pat. No. 1,137,796 (Intermediates for Analgesics), J. Med. Chemistry 290-294, 1969 (Antihypertensives, C.A. 70, 106,447m, 1969), German Offenlegungsschrift No. 2,658,896 (Antidepressants) and Japanese Patent Publication No. 81,029,676 (Anticonvulsants, C.A. 95, 80,985z, 1981).

Novel compounds of the formula I

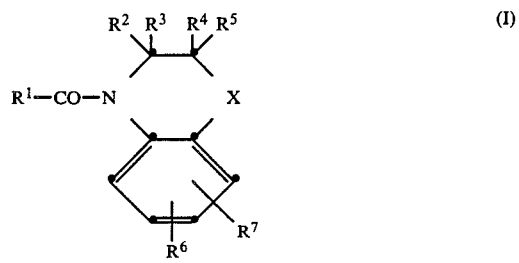

are those in which X is oxygen, sulfur, —SO— or —SO$_2$—; $R^1$ is $C_1-C_6$-cyanoalkyl, $C_2-C_6$-halogenoalkenyl or $C_1-C_6$-alkyl which is substituted by at least two halogen atoms; $R^2$ and $R^5$ independently of one another are hydrogen, $C_1-C_4$-alkyl, $C_1-C_4$-halogenoalkyl, $C_2-C_4$-alkenyl, $C_2-C_4$-alkynyl or $C_2-C_4$-alkoxyalkyl; $R^3$ and $R^4$ independently of one another are hydrogen, $C_2-C_4$-alkenyl, $C_2-C_4$-alkynyl, cyano, $C_2-C_4$-alkoxyalkyl, —COOR$^8$, —CO—NR$^9$R$^{10}$ or $C_1-C_4$-alkyl which is unsubstituted or substituted by halogen, cyano or —CO—A; $R^6$ and $R^7$ independently of one another are hydrogen, halogen, $C_1-C_4$-alkyl, $C_1-C_4$-alkoxy, $C_1-C_4$-halogenoalkyl or $C_1-C_4$-halogenoalkoxy; A is $C_1-C_4$-alkyl, $C_2-C_4$-alkenyl, $C_1-C_4$-alkoxy, $C_3-C_4$-alkenyloxy, $C_3-C_4$-alkynyloxy or —NR$^{11}$R$^{12}$; $R^8$, $R^{10}$ and $R^{12}$ independently of one another are hydrogen, $C_1-C_4$-alkyl, $C_3-C_4$-alkenyl, $C_3-C_4$-alkynyl or $C_3-C_4$-alkoxyalkyl; and $R^9$ and $R^{11}$ independently of one another are hydrogen, $C_1-C_4$-alkyl, $C_3-C_4$-alkenyl, $C_1-C_4$-alkoxy, $C_3-C_4$-alkynyl or $C_3-C_4$-alkoxyalkyl, it being also possible for $R^9$ and $R^{10}$ and also $R^{11}$ and $R^{12}$, together with the nitrogen atom linking them, to form a 5-membered or 6-membered saturated heterocyclic structure which can, if desired, contain an oxygen or sulfur atom or an —NH— or —N($C_1-C_4$-alkyl)-bridge as a member of the ring.

Novel compounds which are preferred in respect of their safener effect are those in which either
(a) X is oxygen, or
(b) $R^1$ is $C_2-C_6$-halogenoalkenyl or $C_1-C_6$-alkyl which is substituted by at least two halogen atoms, or
(c) $R^2$ and $R^5$ are hydrogen, or
(d) $R^3$ and $R^4$ independently of one another are hydrogen, $C_1-C_4$-alkyl, $C_1-C_4$-alkoxycarbonylmethyl or $C_1-C_4$-alkoxycarbonyl, or
(e) $R^6$ and $R^7$ independently of one another are hydrogen or $C_1-C_4$-alkyl.

Preferred novel compounds are, from group b, those in which $R^1$ is $C_1-C_4$-alkyl which is substituted by at least two halogen atoms, and, from group d, those in which $R^3$ and $R^4$ independently of one another are hydrogen or methyl.

Novel compounds of the formula I which form a particularly preferred group are those in which X is oxygen, $R^1$ is $C_2-C_6$-halogenoalkenyl or $C_1-C_4$-alkyl which is substituted by at least two halogen atoms, $R^2$ and $R^5$ are hydrogen, $R^3$ and $R^4$ independently of one another are hydrogen, $C_1-C_4$-alkyl, $C_1-C_4$-alkoxycarbonylmethyl or $C_1-C_4$-alkoxycarbonyl and $R^6$ and $R^7$ independently of one another are hydrogen or $C_1-C_4$-alkyl.

Amongst these, a further outstanding group is formed by the novel compounds in which $R^1$ is $C_1-C_4$-alkyl which is substituted by at least two halogen atoms, and $R^3$, $R^4$, $R^6$ and $R^7$ independently of one another are hydrogen or methyl.

The following preferred novel individual compounds should be mentioned: 4-dichloroacetyl-2,3-dihydro-3,5-dimethyl-1,4-benzoxazine, 4-dichloroacetyl-2,3-dihydro-3-methyl-1,4-benzoxazine and 4-(2-chloropropionyl)-2,3-dihydro-3-methyl-1,4-benzoxazine.

These novel compounds are prepared by reacting an acyl halide of the formula II

$$R^1\text{—CO—Hal} \quad (II)$$

in which $R^1$ is $C_1$–$C_6$-cyanoalkyl, $C_2$–$C_6$-halogenoalkyl or $C_1$–$C_6$-alkyl which is substituted by at least two halogen atoms, and Hal is chlorine or bromine, in the presence of an acid-binding agent with an amine of the formula III

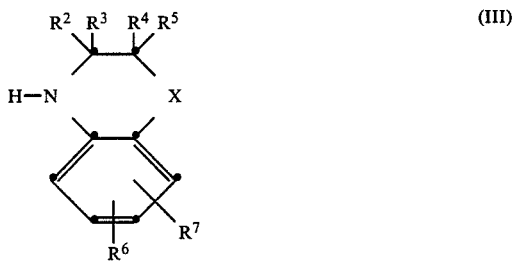

(III)

in which $R^2$, $R^3$, $R^4$, $R^5$, $R^6$, $R^7$ and X are as defined under formula I.

The reaction is advantageously carried out under normal pressure in a solvent inert towards the reaction. Examples of suitable solvents are aliphatic or aromatic hydrocarbons, such as benzene, toluene, xylenes, cyclohexane or petroleum ether, halogenated hydrocarbons, such as chlorobenzene, methylene chloride, ethylene chloride or chloroform, ethers and ether-like compounds, such as diethyl ether, diisopropyl ether, t-butyl methyl ether, dimethoxyethane, dioxane, tetrahydrofuran or anisole; ketones, such as acetone or methyl ethyl ketone; esters, such as ethyl acetate and butyl acetate, and mixtures of such solvents with one another.

Suitable acid-binding agents are, in particular, tertiary amines, such as trimethylamine, triethylamine, quinuclidine, 1,4-diazabicyclo(2,2,2)octane, 1,5-diazabicyclo-(4,3,0)non-5-ene or 1,5-diazabicyclo(5,4,0)undec-7-ene. It is also possible, however, to use inorganic bases, such as hydrides, such as sodium hydride or calcium hydride, hydroxides, such as sodium hydroxide and potassium hydroxide, carbonates, such as sodium carbonate and potassium carbonate or bicarbonates, such as potassium bicarbonate and sodium bicarbonate.

The starting compounds of the formulae II and III are generally known and can be prepared by methods which are known per se.

Depending on the purpose for which it is used, a counter-agent or antidote of the formula I can be employed for pretreating the seed of the cultivated plant (dressing the seed or cuttings), or can be applied to the soil before or after sowing. It can, however, also be applied on its own or together with the herbicide before or after the emergence of the plants. In principle, therefore, the treatment of the plant or the seed with the antidote can be effected independently of the time when the phytotoxic chemical is applied. The treatment of the plant can, however, also be effected by the simultaneous application of the phytotoxic chemical and the counter-agent (tank mixture). Pre-emergence treatment includes both the treatment of the cultivated areas before sowing (ppi = pre plant incorporation) and the treatment of the cultivated areas which have been sown, but are not yet covered with green vegetation.

The amount of the counter-agent applied, in relation to the herbicide, depends largely on the mode of application. In a field treatment, in which the herbicide and the counter-agent are either applied simultaneously (tank mixture) or are applied separately, the ratio of the amount of counter-agent to that of herbicide is within the range from 1:100 to 5:1. As a rule, the full protective action is achieved at a ratio of counter-agent to herbicide of 1:5 to 1:50. In seed dressing and similar selective protective measures, however, much smaller amounts of counter-agent are required in comparison with the amounts of herbicide used later per hectare of cultivated area. In general, 0.1–10 g of counter-agent per kg of seed are required in seed dressing. As a rule, the full protective action is achieved at a level as low as 0.1–5 g of counter-agent per kg of seed. If the counter-agent is to be applied by seed soaking shortly before sowing, it is advantageous to use solutions of the counter-agent containing the active compound in a concentration of 1–10,000 ppm. As a rule, the full protective action is achieved using concentrations of 100–1,000 ppm of the counter-agent.

As a rule, there is a fairly long period of time between protective measures, such as seed dressing and the treatment of cuttings with a counter-agent of the formula I, and the possible later field treatment with agricultural chemicals. In agriculture, horticulture and forestry, pretreated seed and plant material can later come into contact with various chemicals. The invention also relates, therefore, to protective compositions, for cultivated plants, containing, as the active substance, a counter-agent of the formula I together with customary carriers. Compositions of this type can, if desired, additionally contain the agricultural chemicals exerting the effect against which the cultivated plant is to be protected.

Within the scope of the present invention, cultivated plants are to be considered as any plants which produce, in any form, harvested materials, such as seeds, roots, stalks, tubers, leaves, flowers and contained substances, such as oils, sugar, starch, protein etc., and which are cultivated for this purpose. These plants include, for example, all species of cereals, such as wheat, rye, barley and oats as well as, in particular, rice, cultivated millet, maize, cotton, sugar beet, sugar cane, soya, beans and peas.

The counter-agent can be employed in all cases where a cultivated plant of the type mentioned above is to be protected against the harmful action of an agricultural chemical. Possible agricultural chemicals in this sense are primarily herbicides of a very wide variety of classes of substances, but particularly halogenoacetanilides and thiocarbamates.

Halogenoacetanilides exerting a harmful action against cultivated plants which can be counteracted by means of the acylamide derivatives of the formula I are already known in large numbers. Halogenoacetanilides of this type can be described by the following general formula IV

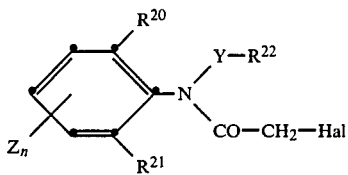 (IV)

In this formula, Hal is halogen, in particular chlorine or bromine, $R^{20}$ and $R^{21}$ independently of one another are each hydrogen, halogen or lower alkyl, alkoxy, alkylthio, halogenoalkyl, alkoxyalkyl or alkylthioalkyl, Z is hydrogen, halogen or lower alkyl, alkoxy, alkylthio, halogenoalkyl, alkoxyalkyl or alkylthioalkyl, the abovementioned radicals Z being preferably in the 3-position in relation to the nitrogen atom, n is 0 to 3, Y is alkylene, especially methylene or 1,1-ethylene and 1,2-ethylene, it being possible for 1,2-ethylene to be substituted by 1–2 lower alkyl groups, and $R^{22}$ is lower alkoxy, hydroxycarbonyl, alkoxycarbonyl, carbamoyl, N-alkylcarbamoyl, N,N-dialkylcarbamoyl, cyano, a substituted or unsubstituted, nitrogen-containing, heterocyclic radical, alkanoyl, substituted or unsubstituted benzoyl or substituted or unsubstituted 1,3,4-oxadiazol-2-yl, 1,3,4-thiadiazol-2-yl, 1,3,4-triazol-3-yl or 1,3,4-triazol-1-yl.

The following may be mentioned as examples of individual representatives of such halogenoacetanilides: N-ethoxymethyl-N-chloroacetyl-2-ethyl-6-methylaniline, N-chloroacetyl-N-methoxymethyl-2,6-diethylaniline, N-chloroacetyl-N-(2-methoxyethyl)-2,6-dimethylaniline, N-(2-allyloxyethyl)-N-chloroacetyl-2,6-dimethylaniline, N-chloroacetyl-N-(2-n-propoxyethyl)-2,6-dimethylaniline, N-chloroacetyl-N-(2-isopropoxyethyl)-2,6-dimethylaniline, N-chloroacetyl-N-(2-methoxyethyl)-2-ethyl-6-methylaniline, N-chloroacetyl-N-(methoxyethyl)-2,6-diethylaniline, N-(2-ethoxyethyl)-N-chloroacetyl-2-ethyl-6-methylaniline, N-chloroacetyl-N-(2-methoxy-1-methylethyl)-2-methylaniline, N-chloroacetyl-N-(2-methoxy-1-methylethyl)-2,6-dimethylaniline, N-chloroacetyl-N-(2-methoxy-1-methylethyl)-2,6-diethylaniline, N-chloroacetyl-N-(2-methoxy-1-methylethyl)-2-ethyl-6-methylaniline, N-(2-ethoxyethyl)-N-chloroacetyl-2,6-diethylaniline, N-chloroacetyl-N-(2-n-propoxyethyl)-2-ethyl-6-methylaniline, N-chloroacetyl-N-(2-n-propoxyethyl)-2,6-diethylaniline, N-chloroacetyl-N-(2-isopropoxyethyl)-2-ethyl-6-methylaniline, N-ethoxycarbonylmethyl-N-chloroacetyl-2,6-dimethylaniline, N-ethoxycarbonyl-methyl-N-chloroacetyl-2,6-diethylaniline, N-chloroacetyl-N-methoxycarbonylmethyl-2,6-dimethylaniline, N-chloroacetyl-N-(2,2-diethoxyethyl)-2,6-dimethylaniline, N-chloroacetyl-N-(2-methoxy-1-methylethyl)-2,3-dimethylaniline, N-(2-ethoxyethyl)-N-chloroacetyl-2-methylaniline, N-chloroacetyl-N-(2-methoxyethyl)-2-methylaniline, N-chloroacetyl-N-(2-methoxy-2-methylethyl)-2,6-dimethylaniline, N-(2-ethoxy-2-methylethyl)-N-chloroacetyl-2-ethyl-6-methylaniline, N-chloroacetyl-N-(1-ethyl-2-methoxyethyl)-2,6-dimethylaniline, N-chloroacetyl-N-(2-methoxyethyl)-2-methoxy-6-methylaniline, N-n-butoxymethyl-N-chloroacetyl-2-tert.-butylaniline, N-(2-ethoxyethyl-1-methylethyl)-2,6-dimethylaniline, N-chloroacetyl-N-(2-methoxyethyl)-2-chloro-6-methylaniline, N-(2-ethoxyethyl)-N-chloroacetyl-2-chloro-6-methylaniline, N-(2-ethoxyethyl)-N-chloroacetyl-2,3,6-trimethylaniline, N-chloroacetyl-1-(2-methoxyethyl)-2,3,6-trimethylaniline, N-chloroacetyl-N-cyanomethyl-2,6-dimethylaniline, N-but-3-in-1-yl-N-chloroacetylaniline, N-chloroacetyl-N-propargyl-2-ethyl-6-methylaniline, N-chloroacetyl-N-(1,3-dioxolan-2-ylmethyl)-2,6-dimethylaniline, N-chloroacetyl-N-(1,3-dioxolan-2-yl-methyl)-2-ethyl-6-methylaniline, N-chloroacetyl-N-(1,3-dioxan- 2-ylmethyl)-2-ethyl-6-methylaniline, N-chloroacetyl-N-(2-furanylmethyl)-2,6-dimethylaniline, N-chloroacetyl-N-(2-furanylmethyl)-2-ethyl-6-methylaniline, N-chloroacetyl-N-(2-tetrahydrofuranylmethyl)-2,6-dimethylaniline, N-chloroacetyl-N-(N-propargylcarbamoylmethyl)-2,6-dimethylaniline, N-chloroacetyl-N-(N,N-dimethylcarbamoylmethyl)-2,6-dimethylaniline, N-(n-butoxymethyl)-N-chloroacetyl-2,6-diethylaniline, N-(2-n-butoxyethyl)-N-chloroacetyl-2,6-diethylaniline, N-chloroacetyl-N-(2-methoxy-1,2-dimethylethyl)-2,6-dimethylaniline, N-chloroacetyl-N-isopropyl-2,3-dimethylaniline, N-chloroacetyl-N-isopropyl-2-chloroaniline, N-chloroacetyl-N-(1H-pyrazol-1-ylmethyl)-2,6-dimethylaniline, N-chloroacetyl-N-(1H-pyrazol-1-ylmethyl)-2-ethyl-6-methylaniline, N-chloroacetyl-N-(1H-1,2,4-triazol-1-ylmethyl)-2,6-dimethylaniline, N-chloroacetyl-N-(1H-1,2,4-triazol-1-ylmethyl)-2,6-diethylaniline, N-benzoylmethyl-N-chloroacetyl-2,6-dimethylaniline, N-benzoylmethyl-N-chloroacetyl-2-ethyl-6-methylaniline, N-chloroacetyl-N-(5-methyl-1,3,4-oxadiazol-2-yl)-2,6-diethylaniline, N-chloroacetyl-N-(5-methyl-1,3,4-oxadiazol-2-yl)-2-ethyl-6-methylaniline, N-chloroacetyl-N-(5-methyl-1,3,4-oxadiazol-2-yl)-2-tert.-butylaniline, N-chloroacetyl-N-(4-chlorobenzoylmethyl)-2,6-dimethylaniline and N-chloroacetyl-N-(1-methyl-5-methylthio-1,3,4-triazol-2-ylmethyl)-2,6-diethylaniline.

Further halogenoacetanilides exerting a harmful action, on cultivated plants, which can be counteracted by the new acylamide derivatives of the formula I are listed in R. Wegler, Chemie der Pflanzenschutz- und Schädlingsbekämpfungsmittel ("The Chemistry of Plant Protection Compositions and Pest Control Compositions"), volume 8, pages 90–93 and pages 322–327.

Thiolcarbamates having a herbicidal action, and exering a phytotoxic action against which cultivated plants can be protected by means of the novel acylamide derivatives of the formula I, have also already been disclosed in large numbers. The protective action of the novel acylamide derivatives of the formula I can be utilised advantageously, particularly when thiolcarbamates are employed in cereals, rice or grafted sorghum.

The thiolcarbamates which exert a phytotoxic action against which cultivated plants, such as cereals, rice and grafted sorghum, can preferably be protected, have the general formulae V and VI:

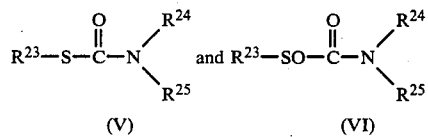

(V)      (VI)

In these formulae, $R^{23}$ is lower alkyl, alkenyl, chloroallyl, dichloroallyl, trichloroallyl, benzyl or 4-chlorobenzyl, $R^{24}$ is $C_2$–$C_4$-alkyl and $R^{25}$ is $C_2$–$C_4$-alkyl or cyclohexyl, it being possible for the radicals $R^{24}$ and $R^{25}$, together with the nitrogen atom to which they are attached, to form a hexahydro-1H-azepine, decahydroquinoline or 2-methyldecahydroquinoline ring.

The following may be mentioned as examples of individual representatives of such thiolcarbamates: S-ethyl N,N-dipropylthiolcarbamate, S-ethyl N,N-diisobutylthiolcarbamate, S-2,3-dichloroallyl N,N-diisopropylthiolcarbamate, S-propyl N-butyl-N-ethylthiolcarbamate, S-2,3,3-trichloroallyl N,N-diisopropylthiolcarbamate, S-propyl N,N-dipropylthiolcarbamate, S-ethyl N-ethyl-N-cyclohexylthiolcarbamate, S-ethyl N-hexahydro-1H-azepine-1-carbothioate, S-isopropyl N,N-hexamethylenethiolcarbamate, S-(p-chlorobenzyl) N,N-diethylthiolcarbamate, N-ethylthiocarbonyl-cis-decahydroquinoline, N-propylthiocarbonyl-decahydroquinaldine, S-ethyl N,N-bis-(n-butyl)-thiolcarbamate and S-tert.-butyl N,N-bis-(n-propyl)-thiolcarbamate.

In addition to the chloroacetanilides and thiolcarbamates, herbicides of other classes of substances are also suitable, for example:

Triazines and triazinones: 2,4-bis-(isopropylamino)-6-methylthio-1,3,5-triazine ("prometryn"), 2,4-bis-(ethylamino)-6-methylthio-1,3,5-triazine ("simetryn"), 2-(1',2'-dimethylpropylamino)-4-ethylamino-6-methylthio-1,3,5-triazine ("dimethametryn"), 4-amino-6-tert.-butyl-4,5-dihydro-3-methylthio-1,2,4-triazin-5-one ("metribuzin"), 2-chloro-4-ethylamino-6-isopropylamino-1,3,5-triazine ("atrazine"), 2-chloro-4,6-bis-(ethylamino)-1,3,5-triazine ("simazine"), 2-tert.-butylamino-4-chloro-6-ethylamino-1,3,5-triazine ("terbuthylazin"), 2-tert.-butylamino-4-ethylamino-6-methoxy-1,3,5-triazine ("terbumeton"), 2-tert.-butylamino-4-ethylamino-6-methylthio-1,3,5-triazine ("terbutryn"), 2-ethylamino-4-isopropylamino-6-methylthio-1,3,5-triazine ("ametryn") and 3,4-bis-(methylamino)-6-tert.-butyl-4,5-dihydro-1,2,4-triazin-5-one.

Ureas: 1-(benzothiazol-2-yl)-1,3-dimethylurea; phenylureas, for example:3-(3-chloro-p-tolyl)-1,1-dimethylurea ("chlorotoluron"), 1,1-dimethyl-3-(α,α,α-trifluoro-m-tolyl)-urea ("fluometuron"), 3-(4-bromo-3-chlorphenyl)-1-methoxy-1-methylurea ("chlorbromuron"), 3-(4-bromophenyl)-1-methoxy-1-methylurea ("metobromuron"), 3-(3,4-dichlorophenyl)-1-methoxy-1-methylurea ("linuron"), 3-(4-chlorophenyl)-1-methoxy-1-methylurea ("monolinuron"), 3-(3,4-dichlorophenyl)-1,1-dimethylurea ("diuron"), 3-(4-chlorophenyl)-1,1-dimethylurea ("monuron") and 3-(3-chloro-4-methoxyphenyl)-1,1-dimethylurea ("metoxuron"); sulfonylureas, for example:N-(2-chlorophenylsulfonyl)-N'-(4-methoxy-6-methyl-1,3,5-triazin-2-yl)-urea, N-(2-methoxycarbonylphenylsulfonyl)-N'-(4,6-dimethylpyrimidin-2-yl)-urea, N-(2,5-dichlorophenylsulfonyl)-N'-(4,6-dimethoxypyrimidin-2-yl)-urea and N-[2-(2-butenyloxy)-phenylsulfonyl]-N'-(4-methoxy-6-methyl-1,3,5-triazin-2-yl)-urea and also the sulfonyl ureas mentioned in European Patent Publications Nos. 44,808 and 44,809.

Chloroacetamides: N-[1-isopropyl-2-methylprop-1-en-1-yl]-N-(2'-methoxyethyl)-chloroacetamide.

Diphenyl ethers and nitrodiphenyl ethers: 2,4-dichlorophenyl 4'-nitrophenyl ether ("nitrofen"), 2-chloro-1-(3'-ethoxy-4'-nitrophenoxy)-4-trifluoromethylbenzene ("Oxyfluorfen"), 2',4'dichlorophenyl 3-methoxy-4-nitrophenyl ether ("Chlormethoxynil"), methyl 2-[4'-(2'',4''-dichlorophenoxy)phenoxy]-propionate, N-(2'-phenoxyethyl)-2-[5'(2''-chloro-4''-trifluoromethylphenoxy)-phenoxy]-propionamide, 2-methoxyethyl 2-[nitro-5-(2-chloro-4-trifluoromethylphenoxy)-phenoxy]-propionate and 2-chloro-4-trifluoromethylphenyl 3'-oxazolin-2'-yl-4'-nitrophenyl ether.

Benzoic acid derivatives: methyl 5-(2',4'-dichlorophenoxy)-2-nitrobenzoate ("Bifenox"), 5-(2'-chloro-4'-trifluoromethylphenoxy)-2-nitrobenzoic acid ("Acifluorfen") and 2,6-dichlorobenzonitrile ("dichlorbenil").

Nitroanilines: 2,6-dinitro-N,N-dipropyl-4-trifluoromethylaniline ("trifluralin") and N-(1'-ethylpropyl)-2,6-dinitro- 3,4-xylidine ("Pendimethalin").

Oxadiazolones: 5-tert.-butyl-3-(2',4'-dichloro-5'-isopropoxyphenyl)-1,3,4-oxadiazol-2-one ("Oxadiazon").

Phosphates: S-2-methylpiperidinocarbonylmethyl 0,0-dipropyl phosphorodithioate ("Piperophos").

Pyrazoles: 1,3-dimethyl-4-(2',4'-dichlorobenzoyl)-5-(4'-tolylsulfonyloxy)-pyrazole.

Also α-(phenoxyphenoxy)-propionic acid derivatives and α-pyridyl-2-oxyphenoxy)-propionic acid derivatives.

Unless it is used to dress seed, the amount of the counter-agent applied varies between about 0.01 and about 5 parts by weight per part by weight of herbicide. The most suitable ratio based on optimum action on the particular cultivated plant is determined on a case by case basis, i.e. depending on the type of herbicide used.

The invention also relates to a process for selectively controlling weeds in crops of cultivated plants, the crops of cultivated plants, parts of the cultivated plants or areas cultivated for cultivated plants being treated with a herbicide and a compound of the formula I or a composition containing this combination. The compositions containing the herbicide/antidote combination also form a part of the present invention.

The weeds to be controlled can be either monocotyledonous or dicotyledonous weeds.

Various methods and techniques are suitable for using compounds of the formula I or compositions containing them in order to protect cultivated plants against the harmful effects of agricultural chemicals, for example the following methods and techniques:

(i) Seed dressing (a) Dressing the seed with an active substance, formulated as a wettable powder, by shaking in a vessel until uniform distribution over the surface of the seed is achieved (dry dressing). In this procedure, about 10 to 500 g of active substance of the formula I (40 g to 2 kg of wettable powder) are used per 100 kg of seed.

(b) Dressing the seed with an emulsion concentrate of the active substance of the formula I by method (a) (wet dressing).

(c) Dressing by immersing the seed in a liquor containing 50–3,200 ppm of an active substance of the formula I for 1 to 72 hours and, if desired, subsequently drying the seed (immersion dressing).

Dressing the seed or treating the sprouted seedling are, of course, the preferred methods of application, because the treatment with active substance is directed entirely towards the target crop. As a rule, 10 g to 500 g, preferably 50 to 250 g, of active substance are used per 100 kg of seed, and, depending on the method employed, which also enables other active substances or micro-nutrients to be added, it is possible to exceed or to use less than the limiting concentrations indicated (repeat dressing).

(ii) Application from a tank mixture

A liquid formulation of a mixture of counter-agent and herbicide (ratio of the one to the other between 10:1 and 1:30) is used, the application rate of herbicide being 0.1 to 10 kg per hectare. A tank mixture of this type is preferably applied before or immediately after sowing or is worked 5 to 10 cm deep into the soil before sowing.

(iii) Application to the seed furrow

The counter-agent is introduced, in the form of an emulsion concentrate, wettable powder or granules, into the open, sown seed furrow and then, after the seed furrow has been covered in a normal manner, the herbicide is applied by the pre-emergence process.

(iv) Controlled release of active substance

A solution of the active substance is absorbed onto mineral granular carriers or polymerised granules (urea formaldehyde) and is allowed to dry. If desired, it is possible to apply a coating (coated granules) which enables the active substance to be released in a metered manner over a specific period of time.

The compounds of the formula I are employed in an unaltered form or, preferably, together with the adjuncts conventionally used in the art of formulation and are, therefore, processed in a known manner to give, for example, emulsion concentrates, solutions which can be atomised or diluted without further treatment, dilute emulsions, wettable powders, soluble powders, dusts, granules and also encapsulations in, for example, polymeric substances. The application processes, such as atomising, nebulising, dusting, sprinkling or watering, are selected to suit the intended aims and the given circumstances, as is also the nature of the compositions.

The formulations, i.e. the compositions, preparations or combinations containing the active substance of the formula I and, if appropriate, a solid or liquid adjuvant, are prepared in a known manner, for example by intimately mixing and/or grinding the active substances with extenders, for example solvents, solid carriers and, if appropriate, surface-active compounds (surfactants).

The following can be suitable as solvents: aromatic hydrocarbons, preferably the fractions from $C_8$ to $C_{12}$, for example mixed xylenes or substituted naphthalenes, phthalic acid esters, such as dibutyl or dioctyl phthalate, aliphatic hydrocarbons, such as cyclohexane or paraffins, alcohols and glycols and also ethers and esters thereof, such as ethanol, ethylene glycol or ethylene glycol monomethyl or monoethyl ether, ketones, such as cyclohexanone, strongly polar solvents, such as N-methyl-2-pyrrolidone, dimethyl sulfoxide or dimethylformamide, and epoxidised or unexpoxidised vegetable oils, such as epoxidised coconut oil or soya oil; or water.

The solid carriers used, for example for dusts and dispersible powders, are, as a rule, natural ground minerals, such as calcite, talc, kaolin, montmorillonite or attapulgite. It is also possible to add highly disperse silica or highly disperse absorbent polymers in order to improve the physical properties. Suitable particulate, adsorptive granular carriers are porous types, for example pumice stone, broken brick, sepiolite or bentonite, while examples of suitable non-sorptive carriers are calcite or sand. In addition, it is possible to use a large number of pregranulated materials of an inorganic or organic nature, such as, in particular, dolomite or comminuted plant residues.

Depending on the nature of the active substance of the formula I to be formulated, suitable surface-active compounds are nonionic, cationic and/or anionic surfactants having good emulsifying, dispersing and wetting properties. Surfactants are also to be understood as meaning mixtures of surfactants.

Suitable anionic surfactants can be so-called water-soluble soaps as well as water-soluble synthetic surface-active compounds.

Examples of soaps are the alkali metal salts, alkaline earth metal salts or substituted or unsubstituted ammonium salts of higher fatty acids ($C_{10}$–$C_{22}$), for example the Na or K salts of oleic or stearic acid, or of natural mixtures of fatty acids, which can be obtained, for example, from coconut oil or tallow oil. Furthermore, mention should also be made of the salts of fatty acid methyltaurides.

More frequently, however, so-called synthetic surfactants are used, in particular fatty sulfonates, fatty sulfates, sulfonated benzimidazole derivatives or alkylarylsulfonates.

The fatty sulfonates or sulfates are, as a rule, in the form of alkali metal salts, alkaline earth metal salts or substituted or unsubstituted ammonium salts and contain an alkyl radical having 8 to 22 C atoms, in which connection alkyl also includes the alkyl moiety of acyl radicals, for example the Na or Ca salt of ligninsulfonic acid, of dodecylsulfuric acid or of a mixture of fatty alcohol sulfates prepared from natural fatty acids. Included under this heading are also the salts of the sulfuric acid esters and sulfonic acids of fatty alcohol/ethylene oxide adducts. The sulfonated benzimidazole derivatives preferably contain 2 sulfonic acid groups and a fatty acid radical having 8–22 C atoms. Examples of alkylarylsulfonates are the Na, Ca or triethanolamine salts of dodecylbenzenesulfonic acid, of dibutylnaphthalenesulfonic acid or of a naphthalenesulfonic acid formaldehyde condensation product.

Furthermore, corresponding phosphates, for example salts of the phosphoric acid ester of a p-nonylphenol/-(4–14)ethylene oxide adduct, or phospholipids are also suitable.

Suitable nonionic surfactants are primarily polyglycol ether derivatives of aliphatic or cycloaliphatic alcohols, saturated or unsaturated fatty acids and alkylphenols; these derivatives can contain 3 to 30 glycol ether groups and 8 to 20 carbon atoms in the (aliphatic) hydrocarbon radical and 6 to 18 carbon atoms in the alkyl radical of the alkylphenols.

Further suitable nonionic surfactants are the water-soluble adducts, containing 20 to 250 ethylene glycol ether groups and 10 to 1,000 propylene glycol ether groups, of polyethylene oxide with polypropylene glycol, ethylenediaminopolypropylene glycol and an alkylpolypropylene glycol having 1 to 10 carbon atoms in the alkyl chain. The said compounds usually contain 1 to 5 ethylene glycol units per unit of propylene glycol.

Examples of nonionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Furthermore, fatty acid esters of polyoxyethylenesorbitan, such as polyoxyethylenesorbitan trioleate, are also suitable.

The cationic surfactants are, in particular, quaternary ammonium salts which contain, as N-substituents, at least one alkyl radical having 8 to 22 C atoms and, as further substituents, lower, halogenated or unhalogenated alkyl radicals, benzyl radicals or lower hydroxyalkyl radicals. The salts are preferably in the form of halides, methylsulfates or ethylsulfates, for example stearyltrimethylammoniumchloride or benzyldi-(2-chloroethyl)-ethylammonium bromide.

The surfactants which are conventional in the art of formulation are described, inter alia, in the following publications:

"McCutcheon's Detergents and Emulsifiers Annual", MC Publishing Corp., Ridgewood, N.J., 1981; H. Stache, "Tensid-Taschenbuch" ("Surfactants Manual"), 2nd edition, C. Hanser Verlag, Munich, Vienna, 1981; M. and J. Ash, "Encyclopedia of Surfactants", vol. I–III, Chemical Publishing Co., New York, 1980–1981.

The agrochemical preparations contain, as a rule, 0.1 to 95%, in particular 0.1 to 80%, of an active substance of the formula I, 1 to 99.9% of a solid or liquid adjuvant and 0 to 25%, in particular 0.1 to 25%, of a surfactant.

In particular, the composition of preferred formulations is as follows: (% =per cent by weight)
Emulsifiable concentrates
  Active substance: 1 to 20%, preferably 5 to 10%
  Surface-active agent: 5 to 30%, preferably 10 to 20%
  Liquid carrier: 50 to 94%, preferably 70 to 85%
Dusts:
  Active substance: 0.1 to 10%, preferably 0.1 to 1%
  Solid carrier: 99.9 to 90%, preferably 99.9 to 99%
Suspension concentrates:
  Active substance: 5 to 75%, preferably 10 to 50%
  Water: 94 to 25%, preferably 90 to 30%
  Surface-active agent: 1 to 40%, preferably 2 to 30%
Wettable powders
  Active substance: 0.5 to 90%, preferably 1 to 80%
  Surface-active agent: 0.5 to 20%, preferably 1 to 15%
  Solid carrier: 5 to 95%, preferably 15 to 90%
Granules
  Active substance: 0.5 to 30%, preferably 3 to 15%
  Solid carrier: 99.5 to 70%, preferably 97 to 85%.

Whereas concentrated compositions are more likely to be preferred as commercial products, the final consumer as a rule uses dilute compositions. The application forms can be diluted down to 0.001% of active substance. The application rates are, as a rule, 0.01 to 10 kg of active substance per hectare, preferably 0.025 to 5 kg of active substance per hectare.

The compositions can also contain further adjuvants, such as stabilisers, anti-foaming agents, viscosity regulators, binders, tackifiers and fertilisers or other active substances for achieving special effects.

In the following examples the temperatures are quoted in degrees centigrade, ° C., and the pressures in millibar, mb.

PREPARATION EXAMPLES

EXAMPLE H1

4-Dichloroacetyl-2,3-dihydro-3-methyl-1,4-benzoxazine. (compound 1.1)

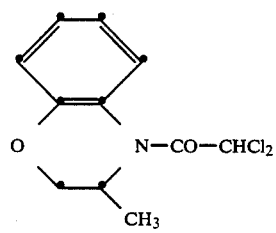

5.3 ml (55 mmoles) of dichloroacetyl chloride are added dropwise, at a temperature of 20° to 25° C. and while stirring, to a suspension of 7.5 g (50 mmoles) of 2,3-dihydro-3-methyl-1,4-benzoxazine and 5.8 g (55 mmoles) of sodium carbonate in 120 ml of benzene. The reaction mixture is then stirred at the same temperature for 30 minutes and is then taken up in a mixture of water and ethyl acetate. The organic phase is washed with saturated sodium chloride solution, dried over sodium sulfate and evaporated. Crystallising the residue from diisopropyl ether gives 10.8 g of 4-dichloroacetyl-2,3-dihydro-3-methyl-1,4-benzoxazine, melting point 105°–107° C.

EXAMPLE H2

4-(2-Chloropropionyl)-2,3-dihydro-3-methyl-1,4-benzoxazine (compound 1.2)

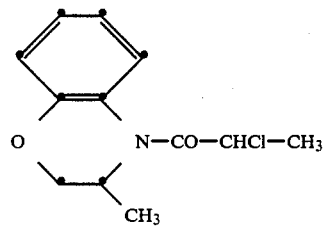

5.35 ml (55 mmoles) of 2-chloropropionyl chloride are added dropwise, at a temperature of 20° to 25° C. and while stirring, to a suspension of 7.5 g (50 mmoles) of 2,3-dihydro-3-methyl-1,4-benzoxazine and 5.8 g (55 mmoles) of sodium carbonate in 120 ml of benzene. The reaction mixture is then stirred at the same temperature for 30 minutes and is then taken up in a mixture of water and ethyl acetate. The organic phase is washed with saturated sodium chloride solution, dried over sodium sulfate and evaporated. Crystallising the residue from diisopropyl ether gives 19.8 g of 4-(2-chloropropionyl)-2,3-dihydro-3-methyl-1,4-benzoxazine, melting point 88°–90° C.

The compounds listed in the following table are obtained analogously.

TABLE 1

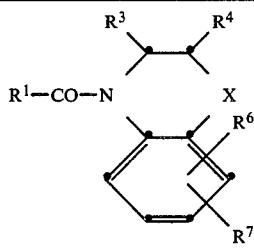

| Compound No. | $R^1$ | X | $R^3$ | $R^4$ | $R^6$ | $R^7$ | Melting point [°C.] |
|---|---|---|---|---|---|---|---|
| 1.1 | $CHCl_2$ | O | $CH_3$ | H | H | H | 105–107 |
| 1.2 | $CH_3$—CHCl— | O | $CH_3$ | H | H | H | 88–90 |
| 1.3 | $CH_2Cl$ | O | $CH_3$ | H | 5-$CH_3$ | H | 78–80 |
| 1.4 | $CH_2Cl$ | O | $CH_3$ | H | H | H | 88–90 |
| 1.5 | $CHCl_2$ | O | H | H | H | H | 94–96 |
| 1.6 | $CH_3$—CHCl— | O | H | H | H | H | <30 |
| 1.7 | $Cl_2C=CCl$— | O | H | H | H | H | <30 |
| 1.8 | $CHCl_2$ | O | H | H | 5-$CH_3$ | H |  |
| 1.9 | $CH_3$—CHCl— | O | H | H | 5-$CH_3$ | H |  |
| 1.10 | $Cl_2C=CCl$— | O | H | H | 5-$CH_3$ | H |  |
| 1.11 | $NC$—$CH_2$— | O | H | H | 5-$CH_3$ | H |  |
| 1.12 | $NC$—$CH_2$— | O | $CH_3$ | H | H | H |  |
| 1.13 | $Cl_2C=CCl$— | O | $CH_3$ | H | H | H | 84–96 |
| 1.14 | $CHCl_2$ | O | $CH_3$ | H | 5-$CH_3$ | H | Oil |
| 1.15 | $CH_3$—CHCl— | O | $CH_3$ | H | 5-$CH_3$ | H | Oil |
| 1.16 | $Cl_2C=CCl$— | O | $CH_3$ | H | 5-$CH_3$ | H |  |
| 1.17 | $CHCl_2$ | O | $CH_3$ | H | 6-$CH_3$ | H | 75–77 |
| 1.18 | $CH_3$—CHCl— | O | $CH_3$ | H | 6-$CH_3$ | H | 49–51 |
| 1.19 | $Cl_2C=CCl$— | O | $CH_3$ | H | 6-$CH_3$ | H | 127–129 |
| 1.20 | $CH_2Cl$— | O | $CH_3$ | H | 6-$CH_3$ | 8-$CH_3$ |  |
| 1.21 | $CHCl_2$— | O | $CH_3$ | H | 6-$CH_3$ | 8-$CH_3$ |  |
| 1.22 | $CH_3$—CHCl— | O | $CH_3$ | H | 6-$CH_3$ | 8-$CH_3$ |  |
| 1.23 | $Cl_2C=CCl$— | O | $CH_3$ | H | 6-$CH_3$ | 8-$CH_3$ |  |
| 1.24 | $CH_2Cl$— | O | H | —$CH_2$—$COOCH_3$ | H | H |  |
| 1.25 | $CHCl_2$— | O | H | —$CH_2$—$COOCH_3$ | H | H |  |
| 1.26 | $CH_3$—CHCl— | O | H | —$CH_2$—$COOCH_3$ | H | H |  |
| 1.27 | $CH_2Cl$ | O | $COOCH_3$ | H | H | H |  |
| 1.28 | $CHCl_2$ | O | $COOCH_3$ | H | H | H |  |
| 1.29 | $CH_3$—CHCl— | O | $COOCH_3$ | H | H | H |  |
| 1.30 | $CH_2Cl$ | O | $COOCH_3$ | H | 5-$CH_3$ | H |  |
| 1.31 | $CHCl_2$ | O | $COOCH_3$ | H | 5-$CH_3$ | H |  |
| 1.32 | $CH_3$—CHCl— | O | $COOCH_3$ | H | 5-$CH_3$ | H |  |
| 1.33 | $Cl_2C=CCl$— | O | $COOCH_3$ | H | 5-$CH_3$ | H |  |
| 1.34 | $CH_2Cl$ | S | $CH_3$ | H | H | H |  |
| 1.35 | $CHCl_2$ | S | $CH_3$ | H | H | H |  |
| 1.36 | $CH_3$—CHCl— | S | $CH_3$ | H | H | H |  |
| 1.37 | $Cl_2C=CCl$— | S | $CH_3$ | H | H | H |  |

Examples of formulations of active substances of the formula I or mixtures of these active substances with herbicides

| Example F1: Wettable powders | (a) | (b) | (c) |
|---|---|---|---|
| Active substance of the formula I or mixture with a herbicide | 20% | 60% | 0.5% |
| Na ligninsulfonate | 5% | 5% | 5% |
| Na laurylsulfate | 3% | — | — |
| Na diisobutylnaphthalenesulfonate | — | 6% | 6% |
| Octylphenol polyethylene glycol ether (7–8 moles of EO) | — | 2% | 2% |
| Highly disperse silica | 5% | 27% | 27% |
| Kaolin | 67% | — | — |
| Sodium chloride | — | — | 59.5% |

The active substance is thoroughly mixed with the adjuvants and the mixture is thoroughly ground in a suitable mill. This gives wettable powders which can be diluted with water to give suspensions of any desired concentration.

| Example F2: Emulsion concentrate | (a) | (b) |
|---|---|---|
| Active substance of the formula I or mixture with a herbicide | 10% | 1% |
| Octylphenol polyethylene glycol ether (4–5 moles of EO) | 3% | 3% |
| Ca dodecylbenzenesulfonate | 3% | 3% |
| Castor oil polyglycol ether (36 moles of EO) | 4% | 4% |
| Cyclohexanone | 30% | 10% |
| Mixed xylenes | 50% | 79% |

Emulsions of any desired concentration can be prepared from this concentrate by dilution with water.

| Example F3: Dusts | (a) | (b) |
|---|---|---|
| Active substance of the formula I or mixture with a herbicide | 0.1% | 1% |
| Talc | 99.9% | — |
| Kaolin | — | 99% |

Ready-to-use dusts are obtained by mixing the active substance with the carrier and grinding the mixture on a suitable mill.

| Example F4: Extruder granules | (a) | (b) |
|---|---|---|
| Active substance of the formula I or mixture with a herbicide | 10% | 1% |
| Na ligninsulfonate | 2% | 2% |
| Carboxymethylcellulose | 1% | 1% |
| Kaolin | 87% | 96% |

The active substance is mixed with the adjuvants and the mixture is ground and moistened with water. This mixture is extruded and then dried in a stream of air.

| Example F5: Coated granules | |
|---|---|
| Active substance of the formula I or mixture with a herbicide | 3% |
| Polyethylene glycol (MW 200) | 3% |
| Kaolin | 94% |

The active substance is finely ground and applied uniformly, in a mixer, to the kaolin, which has been moistened with polyethylene glycol. Dust-free coated granules are obtained in this way.

| Example F6: Suspension concentrate | (a) | (b) |
|---|---|---|
| Active substance of the formula I or mixture with a herbicide | 40% | 5% |
| Ethylene glycol | 10% | 10% |
| Nonylphenol polyethylene glycol ether (15 moles of EO) | 6% | 1% |
| Na ligninsulfonate | 10% | 5% |
| Carboxymethylcellulose | 1% | 1% |
| 37% strength aqueous formaldehyde solution | 0.2% | 0.2% |
| Silicone oil in the form of a 75% strength aqueous emulsion | 0.8% | 0.8% |
| Water | 32% | 77% |

The active substnace is finely ground and intimately mixed with the adjuvants. This gives a suspension concentrate from which suspensions of any desired concentration can be prepared by dilution with water.

| Example F7: Salt solution | |
|---|---|
| Active substance of the formula I or mixture with a herbicide | 5% |
| Isopropylamine | 1% |
| Octylphenol polyethylene glycol ether (78 moles of EO) | 3% |
| Water | 91%. |

BIOLOGICAL EXAMPLES

The capacity of the compounds of the formula I to protect cultivated plants against the phytotoxic action of strong herbicides can be seen from the following example. In the description of the test the compounds of the formula I are designated safeners or counter-agents (antidotes).

EXAMPLE B1

Test with herbicide and counter-agent in maize. The herbicide and the counter-agent are applied together as a tank mixture by the pre-emergence technique.

Plastic containers (25 cm long ×17 cm wide ×12 cm high) are filled with sandy, loamy soil and sown with maize seeds of the variety LG 5. After the seeds have been covered, a dilute solution of the substance to be tested as a safener, and of the herbicide, is sprayed onto the surface of the soil as a tank mixture. The protective action of the safener is evaluated as a percentage 21 days after the application. The references used here are the plants which have been treated only with the herbicide (no protective action) and the completely untreated control (100% protective action).

Test results:
Herbicide: N—Chloroacetyl-N—(2-methoxy-1-methylethyl)-2,6-dimethylaniline.

| Counter-agent | | Herbicide | Relative protective |
|---|---|---|---|
| No. | kg/hectare | kg/hectare | action, [%] |
| 1.1 | 1.5 | 6 | 63 |
| 1.1 | 0.75 | 6 | 63 |
| 1.1 | 1 | 4 | 50 |
| 1.1 | 0.5 | 4 | 63 |
| 1.2 | 1.5 | 6 | 63 |
| 1.2 | 0.75 | 6 | 63 |
| 1.2 | 1 | 4 | 63 |
| 1.2 | 0.5 | 4 | 63 |

What is claimed is:

1. Acylamides of the formula

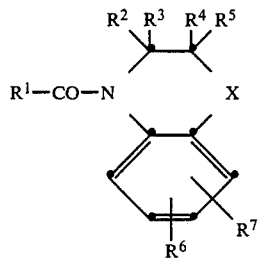

in which X is oxygen, $R^1$ is $C_1-C_6$-cyanoalkyl, $C_2-C_6$-halogenoalkenyl or $C_1-C_6$-alkyl which is substituted by at least two chlorine atoms; $R^2$ and $R^5$ independently of one another are hydrogen, $C_1-C_4$-alkyl, $C_1-C_4$-halogenoalkyl, $C_2-C_4$-alkenyl, $C_2-C_4$-alkynyl or $C_2-C_4$-alkoxyalkyl; $R^3$ and $R^4$ independently of one another are hydrogen, $C_2-C_4$-alkenyl, $C_2-C_4$-alkynyl, cyano, $C_2-C_4$-alkoxyalkyl, —$COOR^8$, —CO—$NR^9R^{10}$ or $C_1-C_4$-alkyl which is unsubstituted or substituted by halogen, cyano or —CO—A; $R^6$ and $R^7$ independently of one another are hydrogen, halogen, $C_1-C_4$-alkyl, $C_1-C_4$-alkoxy, $C_1-C_4$-halogenoalkyl or $C_1-C_4$-halogenoalkoxy, A is $C_1-C_4$-alkyl, $C_2-C_4$-alkenyl, $C_1-C_4$-alkoxy, $C_3-C_4$-alkenyloxy, $C_3-C_4$-alkynyloxy or -$NR^{11}R^{12}$; $R^8$, $R^{10}$ and $R^{12}$ independently of one another are hydrogen, $C_1-C_4$-alkyl, $C_3-C_4$-alkenyl, $C_3-C_4$-alkynyl or $C_3-C_4$-alkoxyalkyl;and $R^9$ and $R^{11}$ independently of one another are hydrogen, $C_1-C_4$-alkyl, $C_3-C_4$-alkenyl, $C_1-C_4$-alkoxy, $C_3-C_4$-alkynyl or $C_3-C_4$-alkoxyalkyl, it being also possible for $R^9$ and $R^{10}$ and also $R^{11}$ and $R^{12}$, together with the nitrogen atom linking them, to form a 5-membered or 6-membered saturated heterocyclic structure which can, optionally, contain an oxygen or sulfur atom or an —NH— or —N($C_1-C_4$-alkyl)- bridge as a member of the ring.

2. A compound according to claim 1, wherein $R^1$ is $C_2-C_6$-halogenoalkenyl or $C_1-C_6$alkyl which is substituted by at least two chlorine atoms.

3. A compound according to claim 1, wherein $R^2$ and $R^5$ are hydrogen.

4. A compound according to claim 1, wherein $R^3$ and $R^4$ independently of one another are hydrogen, $C_1$-$C_4$-alkyl, $C_1$-$C_4$-alkoxycarbonylmethyl or $C_1$-$C_4$-alkoxycarbonyl.

5. A compound according to claim 1, wherein $R^6$ and $R^7$ independently of one another are hydrogen or $C_1$-$C_4$-alkyl.

6. A compound according to claim 4, wherein $R^3$ and $R^4$ independently of one another are hydrogen or methyl.

7. A compound according to claim 2, wherein $R^1$ is $C_1$-$C_4$-alkyl which is substituted by at least two chlorine atoms.

8. A compound according to claim 1, wherein $R^1$ is $C_2$-$C_6$-halogenoalkenyl or $C_1$-$C_4$-alkyl which is substituted by at least two chlorine atoms, $R^2$ and $R^5$ are hydrogen, $R^3$ and $R^4$ independently of one another are hydrogen, $C_1$-$C_4$-alkyl, $C_1$-$C_4$-alkoxycarbonylmethyl or $C_1$-$C_4$-alkoxycarbonyl and $R^6$ and $R^7$ independently of one another are hydrogen or $C_1$-$C_4$-alkyl.

9. A compound according to claim 8, wherein $R^1$ is $C_1$-$C_4$-alkyl which is substituted by at least two chlorine atoms, and $R^3$, $R^4$, $R^6$ and $R^7$ independently of one another are hydrogen or methyl.

10. 4-Dichloroacetyl-2,3-dihydro-3-methyl-1,4-benzoxazine according to claim 1.

11. 4-Dichloroacetyl-2,3-dihydro-3,5-dimethyl-1,4-benzoxazine according to claim 1.

12. 4-(2-Chloropropionyl)-2,3-dihydro-3-methyl-1,4-benzoxazine.

13. A composition for protecting cultivated plants against the phytotoxic action of herbicides, comprising an inert carrier and an acylamide of the formula

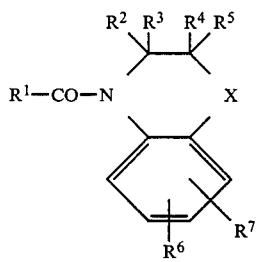

in which X is oxygen, $R^1$ is $C_1$-$C_6$-cyanoalkyl, $C_2$-$C_6$-halogenalkenyl or $C_1$-$C_6$-alkyl which is substituted by at least two chlorine atoms; $R^2$ and $R^5$ independently of one another are hydrogen, $C_1$-$C_4$-alkyl, $C_1$-$C_4$-halogenoalkyl, $C_2$-$C_4$-alkenyl, $C_2$-$C_4$-alkynyl or $C_2$-$C_4$-alkoxyalky; $R^3$ and $R^4$ independently of one another are hydrogen, $C_2$-$C_4$-alkenyl, $C_2$-$C_4$-alkynyl, cyano, $C_2$-$C_4$-alkoxyalkyl, —$COOR^8$, —CO—$NR^9R^{10}$ or $C_1$-$C_4$-alkyl which is unsubstituted or substituted by halogen, cyano or —CO—A; $R^6$ and $R^7$ independently of one another are hydrogen, halogen, $C_1$-$C_4$-alkyl, $C_1$-$C_4$-alkoxy, $C_1$-$C_4$-halogenoalkyl or $C_1$-$C_4$-halogenoalkoxy; A is $C_1$-$C_4$-alkyl, $C_2$-$C_4$-alkenyl, $C_1$-$C_4$-alkoxy, $C_3$-$C_4$-alkenyloxy, $C_3$-$C_4$-alkynyloxy or -$NR^{11}R^{12}$; $R^8$, $R^{10}$ and $R^{12}$ independently of one another are hydrogen, $C_1$-$C_4$-alkyl, $C_3$-$C_4$-alkenyl, $C_3$-$C_4$-alkynyl or $C_3$-$C_4$-alkoxyalkyl; and $R^9$ and $R^{11}$ independently of one another are hydrogen, $C_1$-$C_4$-alkyl, $C_3$-$C_4$-alkenyl, $C_1$-$C_4$-alkoxy, $C_3$-$C_4$-alkynyl or $C_3$-$C_4$-alkoxyalkyl, it being also possible for $R^9$ and $R^{10}$ and also $R^{11}$ and $R^{12}$, together with the nitrogen atom linking them, to form a 5-membered or 6-membered saturated heterocyclic structure which can, optionally, contain an oxygen or sulfur atom or an —NH— or —N($C_1$-$C_4$-alkyl)- bridge as a member of the ring.

14. The composition of claim 13, further comprising a herbicide.

15. The composition of claim 13 or claim 14, wherein $R^1$ is $C_2$-$C_6$-halogenoalkenyl or $C_1$-$C_6$-alkyl which is substituted by at least two chlorine atoms.

16. The composition of claim 13 or claim 14, wherein $R^2$ and $R^5$ are hydrogen.

17. The composition of claim 13 or claim 14, wherein $R^3$ and $R^4$ independently of one another are hydrogen, $C_1$-$C_4$-alkyl, $C_1$-$C_4$-alkoxycarbonylmethyl or $C_1$-$C_4$-alkoxycarbonyl.

18. The composition of claim 13 or claim 14, wherein $R^6$ and $R^7$ independently of one another are hydrogen or $C_1$-$C_4$-alkyl.

19. The composition of claim 17, wherein $R^3$ and $R^4$ independently of one another are hydrogen or methyl.

20. The composition of claim 15, wherein $R^1$ is $C_1$-$C_4$-alkyl which is substituted by at least two chlorine atoms.

21. The composition of claim 13 or 14, wherein $R^1$ is $C_2$-$C_6$-halogenoalkenyl or $C_1$-$C_4$-alkyl which is substituted by at least two chlorine atoms, $R^2$ and $R^5$ are hydrogen, $R^3$ and $R^4$ independently of one another are hydrogen, $C_1$-$C_4$-alkyl, $C_1$-$C_4$-alkoxycarbonylmethyl or $C_1$-$C_4$-alkoxycarbonyl and $R^6$ and $R^7$ independently of one another are hydrogen or $C_1$-$C_4$-alkyl.

22. The composition of claim 21, wherein $R^1$ is $C_1$-$C_4$-alkyl which is substituted by at least two chlorine atoms, and $R^3$, $R^4$, $R^6$ and $R^7$ independently of one another are hydrogen or methyl.

23. The composition of claim 13 or claim 14 wherein the acylamide is 4-dichloroacetyl-2,3-dihydro-3-methyl-1,4-benzoxazine.

24. The composition of claim 13 or claim 14 wherein the acylamide is 4-dichloroacetyl-2,3-dihydro-3,5-dimethyl-1,4-benzoxazine.

25. The composition of claim 13 or claim 14, wherein the acylamide 4-(2-chloropropionyl)-2,3-dihydro-3-methyl-1,4-benzoxazine.

26. A process for selectively controlling weeds in the crops of useful plants, which comprises treating the cultivated plants or the area on which they are cultivated with effective amounts of both a herbicide and an acylamide counter-agent of the formula

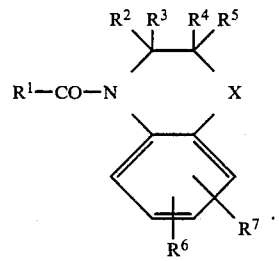

in which X is oxygen, $R^1$ is $C_1$-$C_6$-cyanoalkyl, $C_2$-$C_6$-halogenalkenyl or $C_1$-$C_6$-alkyl which is substituted by at least two chlorine atoms; $R^2$ and $R^5$ independently of one another are hydrogen, $C_1$-$C_4$-alkyl, $C_1$-$C_4$-halogenoalkyl, $C_2$-$C_4$-alkenyl, $C_2$-$C_4$-alkynyl or $C_2$-$C_4$-alkoxyalkyl; $R^3$ and $R^4$ independently of one another are hydrogen, $C_2$-$C_4$-alkenyl, $C_2$-$C_4$-alkynyl, cyano, $C_2$-$C_4$-alkoxyalkyl, —$COOR^8$, —CO—$NR^9R^{10}$ or $C_1$-$C_4$-alkyl which is unsubstituted or substituted by halogen, cyano or —CO—A; $R^6$ and $R^7$ independently of one another are hydrogen, halogen, $C_1$–$C_4$-alkyl, $C_1$–$C_4$-alkoxy, $C_1$–$C_4$-halogenoalkyl or $C_1$–$C_4$-halogenoalkoxy; A is $C_1$–$C_4$-alkyl, $C_2$–$C_4$-alkenyl, $C_1$–$C_4$-alkoxy, $C_3$–$C_4$-alkenyloxy, $C_3$–$C_4$-alkynyloxy or —$NR^{11}R^{12}$; $R^8$, $R^{10}$ and $R^{12}$ independently of one another are hydrogen, $C_1$–$C_4$-alkyl, $C_3$–$C_4$-alkenyl, $C_3$–$C_4$-alkynyl or $C_3$–$C_4$-alkoxyalkyl; and $R^9$ and $R^{11}$ independently of one another are hydrogen, $C_1$–$C_4$-alkyl, $C_3$–$C_4$-alkenyl, $C_1$–$C_4$-alkoxy, $C_3$–$C_4$-alkynyl or $C_3$–$C_4$-alkoxyalkyl, it being also possible for $R^9$ and $R^{10}$ and also $R^{11}$ and $R^{12}$, together with the nitrogen atom linking them, to form a 5-membered or 6-membered saturated heterocyclic structure which can, optionally contain an oxygen or sulfur atom or an —NH— or —N($C_1$–$C_4$-alkyl)-bridge as a member of the ring.

27. A process for protecting cultivated plants against damage occurring in the application of herbicides, which comprises treating either the area cultivated for the plant, before or during the application of the herbicide, or the seed or cuttings of the plants or the plant itself, with an effective amount of an acylamide of the formula

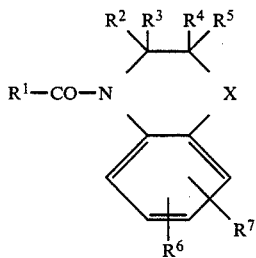

in which X is oxygen, $R^1$ is $C_1$–$C_6$-cyanoalkyl, $C_2$–$C_6$-halogenalkenyl or $C_1$–$C_6$-alkyl which is substituted by at least two chlorine atoms; $R^2$ and $R^5$ independently of one another are hydrogen, $C_1$–$C_4$-alkyl, $C_1$–$C_4$-halogenoalkyl, $C_2$–$C_4$-alkenyl, $C_2$–$C_4$-alkynyl or $C_2$–$C_4$-alkoxyalkyl; $R^3$ and $R^4$ independently of one another are hydrogen, $C_2$–$C_4$-alkenyl, $C_2$–$C_4$-alkynyl, cyano, $C_2$–$C_4$-alkoxyalkyl, —$COOR^8$, —CO—$NR^9R^{10}$ or $C_1$–$C_4$-alkyl which is unsubstituted or substituted by halogen, cyano or —CO—A; $R^6$ and $R^7$ independently of one another are hydrogen, halogen, $C_1$–$C_4$-alkyl, $C_1$–$C_4$-alkoxy, $C_1$–$C_4$-halogenoalkyl or $C_1$–$C_4$-halogenoalkoxy; A is $C_1$–$C_4$-alkyl, $C_2$–$C_4$-alkenyl, $C_1$–$C_4$-alkoxy, $C_3$–$C_4$-alkenyloxy, $C_3$–$C_4$-alkynyloxy or —$NR^{11}R^{12}$; $R^8$, $R^{10}$ and $R^{12}$ independently of one another are hydrogen, $C_1$–$C_4$-alkyl, $C_3$–$C_4$-alkenyl, $C_3$–$C_4$-alkynyl or $C_3$–$C_4$-alkoxyalkyl; and $R^9$ and $R^{11}$ independently of one another are hydrogen, $C_1$–$C_4$-alkyl, $C_3$–$C_4$-alkenyl, $C_1$–$C_4$-alkoxy, $C_3$–$C_4$-alkynyl or $C_3$–$C_4$-alkoxyalkyl, it being also possible for $R^9$ and $R^{10}$ and also $R^{11}$ and $R^{12}$, together with the nitrogen atom linking them, to form a 5-membered or 6-membered saturated heterocyclic structure which can, optionally contain an oxygen or sulfur atom or an —NH— or —N($C_1$–$C_4$-alkyl)- bridge as a member of the ring.

28. The seed of a useful plant which has been treated with a protective amount of an acylamide of the formula

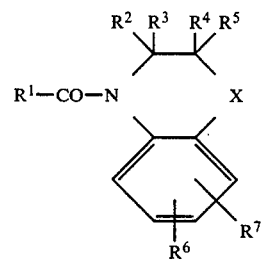

in which X is oxygen, $R^1$ is $C_1$–$C_6$-cyanoalkyl, $C_2$–$C_6$-halogenalkenyl or $C_1$–$C_6$-alkyl which is substituted by at least two chlorine atoms; $R^2$ and $R^5$ independently of one another are hydrogen, $C_1$–$C_4$-alkyl, $C_1$–$C_4$-halogenoalkyl, $C_2$–$C_4$-alkenyl, $C_2$–$C_4$-alkynyl or $C_2$–$C_4$-alkoxyalkyl; $R^3$ and $R^4$ independently of one another are hydrogen, $C_2$–$C_4$-alkenyl, $C_2$–$C_4$-alkynyl, cyano, $C_2$–$C_4$-alkoxyalkyl, —$COOR^8$, —CO—$NR^9R^{10}$ or $C_1$–$C_4$-alkyl which is unsubstituted or substituted by halogen, cyano or —CO—A; $R^6$ and $R^7$ independently of one another are hydrogen, halogen, $C_1$–$C_4$-alkyl, $C_1$–$C_4$-alkoxy, $C_1$–$C_4$-halogenoalkyl or $C_1$–$C_4$-halogenoalkoxy; A is $C_1$–$C_4$-alkyl, $C_2$–$C_4$-alkenyl, $C_1$–$C_4$-alkoxy, $C_3$–$C_4$-alkenyloxy, $C_3$–$C_4$-alkynyloxy or —$NR^{11}R^{12}$; $R^8$, $R^{10}$ and $R^{12}$ independently of one another are hydrogen, $C_1$–$C_4$-alkyl, $C_3$–$C_4$-alkenyl, $C_3$–$C_4$-alkynyl or $C_3$–$C_4$-alkoxyalkyl; and $R^9$ and $R^{11}$ independently of one another are hydrogen, $C_1$–$C_4$-alkyl, $C_3$–$C_4$-alkenyl, $C_1$–$C_4$-alkoxy, $C_3$–$C_4$-alkynyl or $C_3$–$C_4$-alkoxyalkyl, is being also possible for $R^9$ and $R^{10}$ and also $R^{11}$ and $R^{12}$, together with the nitrogen atom linking them, to form a 5-membered or 6-membered saturated heterocyclic structure which can, optionally, contain an oxygen or sulfur atom or an —NH—or —N($C_1$–$C_4$-alkyl)-bridge as a member of the ring.

* * * * *